(12) United States Patent
Qian et al.

(10) Patent No.: US 10,531,870 B2
(45) Date of Patent: Jan. 14, 2020

(54) MULTI-FUNCTIONAL PROTECTIVE SLEEVE FOR WOUND OF SOFT TISSUE DURING OPERATION

(71) Applicant: JIANGSU HAIZE MEDICAL SCIENTIFIC DEVELOPMENT CO., LTD, Wuxi (CN)

(72) Inventors: Jianmin Qian, Wuxi (CN); Yun Sun, Wuxi (CN)

(73) Assignee: JIANGSU HAIZE MEDICAL SCIENTIFIC DEVELOPMENT CO., LTD., Xishan, Wuxi, Jiangsu (CN)

( * ) Notice: Subject to any disclaimer, the term of this patent is extended or adjusted under 35 U.S.C. 154(b) by 310 days.

(21) Appl. No.: 15/587,050

(22) Filed: May 4, 2017

(65) Prior Publication Data

US 2017/0303906 A1 Oct. 26, 2017

Related U.S. Application Data

(63) Continuation of application No. PCT/CN2015/095079, filed on Nov. 20, 2015.

(30) Foreign Application Priority Data

Aug. 21, 2015 (CN) .......................... 2015 1 0517134

(51) Int. Cl.
*A61B 17/02* (2006.01)
*A61B 17/00* (2006.01)
*A61F 13/36* (2006.01)

(52) U.S. Cl.
CPC .... *A61B 17/0218* (2013.01); *A61B 17/00234* (2013.01); *A61B 17/0293* (2013.01);
(Continued)

(58) Field of Classification Search
CPC ..... A61B 17/02; A61B 17/00; A61B 17/0218; A61B 17/0293; A61F 13/36
See application file for complete search history.

(56) References Cited

U.S. PATENT DOCUMENTS 6,814,720 B2 * 11/2004 Olsen ...................... A61F 5/448
337/344
8,088,145 B2 * 1/2012 Zhu .................... A61B 17/0206
606/213
(Continued)

FOREIGN PATENT DOCUMENTS

CN 202027736 U 11/2011
CN 203408104 U 1/2014
(Continued)

OTHER PUBLICATIONS

Jiangsu Haize Medical Scient Dev. Co. Ltd., International Search Report and Written Opinion, PCT/CN2015/095079, dated May 23, 2016, 20 pgs.
(Continued)

*Primary Examiner* — Christopher J Beccia
(74) *Attorney, Agent, or Firm* — Morgan, Lewis & Bockius LLP

(57) ABSTRACT

A multi-functional soft tissue wound protective sleeve includes: a waste collection bag including a bottom patch and a surface patch connected to form a cavity; a bottom ring to be inserted into a human body, to push away human tissues surrounding the bottom ring to form a surgery space; a flip ring located above the waste collection bag and having an adjustable distance with the bottom ring, to prevent waste from touching a surgical surface; a medical inner membrane connecting the bottom ring to the flip ring and defining a surgery channel to the surgery space; a positioning ring sealed with a hole edge of the surgery through-hole on the bottom patch; and a medical outer membrane connecting the
(Continued)

positioning ring to the flip ring so as to guide waste escaping the surgery channel over the flip ring to flow into the waste collection bag.

8 Claims, 8 Drawing Sheets

(52) U.S. Cl.
CPC .... *A61F 13/36* (2013.01); *A61B 2017/00287* (2013.01); *A61B 2017/0225* (2013.01)

(56) References Cited

U.S. PATENT DOCUMENTS

| | | | | |
|---|---|---|---|---|
| 9,492,153 | B2* | 11/2016 | Vaillancourt | ...... A61B 17/0293 |
| 2006/0247498 | A1* | 11/2006 | Bonadio | ............ A61B 17/3423 |
| | | | | 600/208 |
| 2008/0065032 | A1* | 3/2008 | Palmieri | ................. A61F 5/443 |
| | | | | 604/337 |
| 2013/0178709 | A1* | 7/2013 | Suh | .................... A61B 17/0218 |
| | | | | 600/205 |
| 2015/0119647 | A1 | 4/2015 | Vaillantcourt et al. | |

FOREIGN PATENT DOCUMENTS

| | | |
|---|---|---|
| CN | 203597988 U | 5/2014 |
| CN | 204909655 U | 12/2015 |
| CN | 105411682 A | 3/2016 |

OTHER PUBLICATIONS

Jiangsu Haize Medical Scient Dev. Co. Ltd., International Preliminary Report on Patentability, PCT/CN2015/095079, dated Feb. 27, 2018, 7 pgs.

* cited by examiner

MULTI-FUNCTIONAL PROTECTIVE SLEEVE FOR WOUND OF SOFT TISSUE DURING OPERATION

RELATED APPLICATIONS

This application is a continuation application of PCT Patent Application No. PCT/CN2015/095079, entitled "MULTI-FUNCTIONAL PROTECTIVE SLEEVE FOR WOUND OF SOFT TISSUE DURING OPERATION" filed on Nov. 20, 2015, which claims priority to Chinese Patent Application No. 201510517134.5, filed with the Chinese Patent Office on Aug. 21, 2015, and entitled "MULTI-FUNCTIONAL PROTECTIVE SLEEVE FOR WOUND OF SOFT TISSUE DURING OPERATION", both of which are incorporated herein by reference in their entirety.

TECHNICAL FIELD

The present application relates to a medical instrument, and in particular, to a cleanliness protection instrument applicable to a wound, a wound surface, and a surgical environment in a human body surgical operation and a minimally invasive surgery, specifically, a multi-functional soft tissue wound protective sleeve.

BACKGROUND OF THE DISCLOSURE

As is known to all, blood and bacterial fluid mixed with pathogens often overflow to a surgical wound at the abdomen and thorax in a surgical process, causing pollution to a surgical wound and wound surface. Cancer cells or other pollutants that fall off, such as gastric acid, intestinal juice, and bile, may possibly contaminate a surgical wound or wound surface, causing cancer cells to be implanted or surgeries to be damaged. When the overflowing fluid is in large amounts, the fluid may flow to the outside of a body cavity and cause pollution to the environment around a surgical bed and a body surface of an operator.

A traditional solution is covering a surgical wound with an incision protective jacket, to protect wound soft tissues from being polluted by the foregoing fluid. Besides, to prevent fluid in a wound from flowing out and polluting a human body, a water absorption cloth is usually required to cover on a patient, and an opening is disposed at a position, corresponding to a wound, on the water absorption cloth so that a surgical instrument enters. However, a problem that the surgical manner faces is that if overflowing to a wound surface, fluid flowing from a wound may easily permeate to a direction of a surgical wound along the wound surface, polluting the wound surface (the abdomen and thorax, the skin, and sterile cloths), and permeate to the surgical wound from a lower portion of the water absorption cloth, causing pollution to the surgical wound. Therefore, a traditional surgical wound protective jacket cannot prevent fluid overflowing to a surgical surface from polluting a wound and an environment around a surgical bed. For this, the applicant designs a protective jacket with an effluent/waste collection bag, which relatively web resolves a problem of effluent pollution in a surgical process. See the Chinese patent application 2015102034172 for details. However, the patent still has a greatest problem, which is inconvenient adjustment of a distance between a bottom ring and an opening ring, causing that an upper ring cannot be closely fit with a wound surface.

SUMMARY

An objective of the present application is designing a multi-functional soft tissue wound protective sleeve with an adjustable height and capable of accurate positioning specific to a problem of poor universality and inconvenient positioning that an existing surgical incision protective jacket with an effluent collection bag has.

According to technical solutions of the present application, a multi-functional soft tissue wound protective sleeve includes: a waste collection bag including a bottom patch and a surface patch, wherein outer edges of the bottom patch and the surface patch are connected to form a cavity, a surgery through-hole is provided on the bottom patch, and a waste inlet opening is provided on the surface patch; a bottom ring to be inserted into a human body, wherein the bottom ring is configured to push away human tissues surrounding the bottom ring to form a surgery space; a flip ring located above the waste collection bag and having an adjustable distance with the bottom ring, wherein the flip ring is configured to prevent waste from touching a surgical surface; a medical inner membrane connecting the bottom ring to the flip ring and defining a surgery channel to the surgery space; a positioning ring sealed with a hole edge of the surgery through-hole on the bottom patch; and a medical outer membrane connecting the positioning ring to the flip ring, wherein the medical outer membrane guides waste escaping the surgery channel over the flip ring to flow into the waste collection bag.

A plurality of support blocks is disposed between the bottom patch and the surface patch and deployed around the waste inlet opening of the surface patch to prevent the waste collection bag from closing. The support block is a strip sponge filter structure. The waste collection bag includes a diversion component to discharge waste accumulated in the waste collection bag. The bottom ring also uses a structure same as the flip ring. The opening of the surface patch 102 has a wrinkled structure, for waste to flow into the waste collection bag. The protective sleeve according to the present application has a simple structure, reliable positioning, and strong use, and can improve a surgical field and provide a clean surgical environment.

DESCRIPTION OF EMBODIMENTS

The present application is further described with reference to figures and embodiments in the below.

Figure 5:
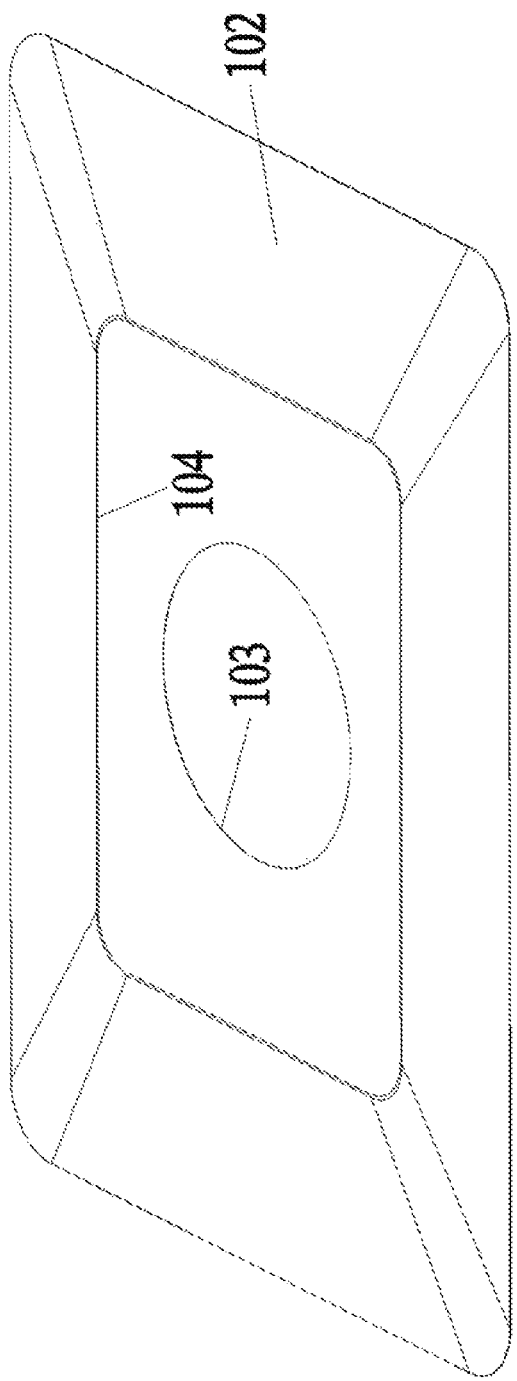
FIG. 5 is a schematic structural diagram of a bag formed by connecting the surface patch and the bottom patch of the multi-functional soft tissue wound protective sleeve according to the present application.

As shown in FIGS. 1 to 8, a multi-functional soft tissue wound protective sleeve includes: a waste collection bag 1, where the waste collection bag 1 consists of a bottom patch 101 (FIG. 3) and a surface patch 102 (FIG. 4), outer edges of the bottom patch 101 and the surface patch 102 are connected to form a bag (as shown in FIG. 5), a surgery through-hole 103 is provided on the bottom patch 101, a waste inlet opening 104 is provided on the surface patch 102, and an area of the waste inlet opening 102 is greater than that of the surgery through-hole 103.

Figure 7:
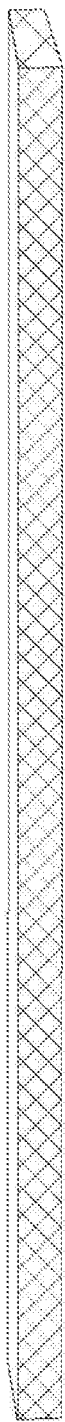
FIG. 7 is a schematic structural diagram of a plurality of support blocks of the multi-functional soft tissue wound protective sleeve according to the present application.

To prevent accumulation in large amounts in a surgical process, a diversion component 9 is connected at an edge of the waste collection bag 1, to discharge overmuch effluent out of the bag in time, and waste can be flown into the bag and is cleared up after a surgery is finished. A plurality of support blocks (2) (as shown in FIG. 7) are deployed around the waste inlet opening 102 of the surface patch 102, to prevent the bottom patch and the surface patch from closing so that waste enters the bag; each support block 2 may use a strip or block sponge filter structure; to prevent a bag opening from changing, an adhesive may be applied to two sides of the support block 2, to adhere the surface patch and the bottom patch, and can be peeled off when needed, so that waste can be stuffed into the bag; in specific implementation, the support block 2 can be omitted. In some embodiments, the support block can be replaced by cushion-loaded medical cotton and gauze, a channel may be formed between the surface patch and a bottom surface by designing an opening as a creased structure, and the opening of the surface patch is not closed on the bottom patch by creasing. Other methods for keeping an effluent inlet fluent may also be used; and if a support block is used, the support block is either designed as a whole strip or designed as multiple small blocks.

In some embodiments, a bottom ring 3 (which may be a medical thermoplastic polyurethanes (TPU) ring) is inserted into a human body, where after being inserted into a human body, the bottom ring 3 pushes human tissues surrounding the bottom ring to form a surgery space; and the bottom ring 3 may use a common circular cross section ring or use an easily turnover structure such as an easily turnover 8 shape or a two-petal shape.

Figure 8:
FIG. 8 is a schematic sectional structural diagram of a flip ring of the multi-functional soft tissue wound protective sleeve according to the present application.

In some embodiments, a flip ring 4 is located above the waste collection bag 1, and can adjust a distance between the flip ring 4 and the bottom ring 3 and can prevent waste from touching a surgical surface, and an inner diameter of the flip ring 4 is less than an inner diameter of the bottom ring; and the flip ring 4 better uses a TPU ring whose cross section is "8"-shaped shown in FIG. 8.

Figure 6:
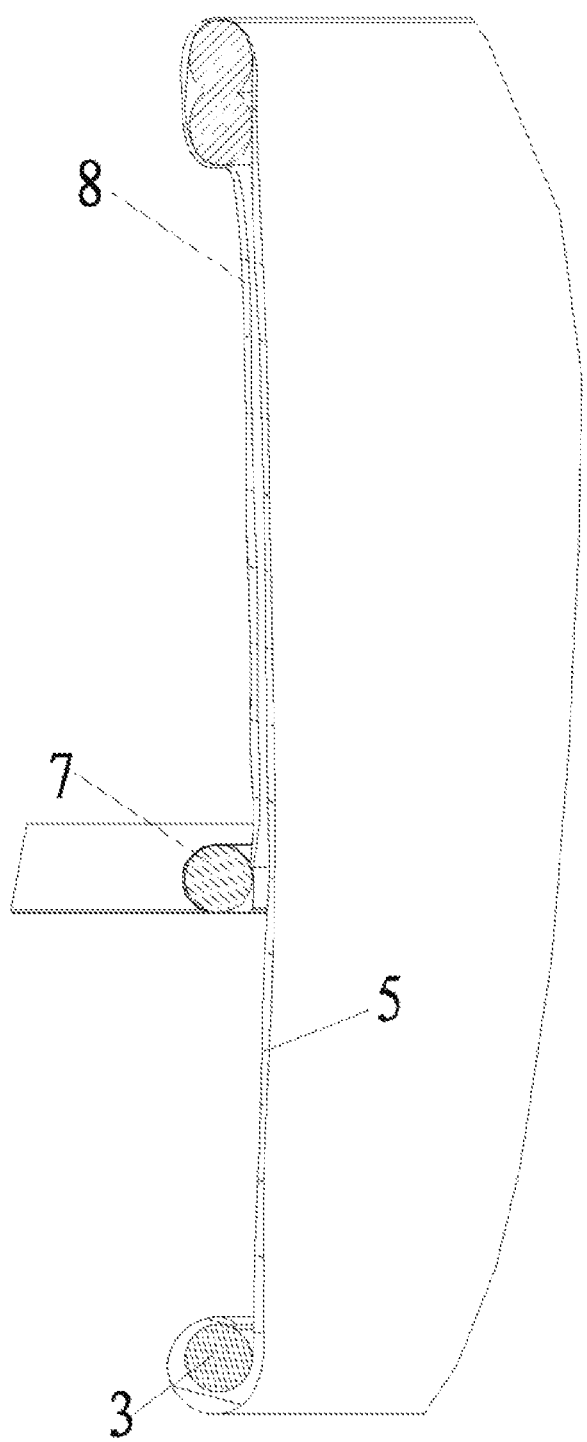
FIG. 6 is a schematic structural diagram of a single sided amplified view of connection relationships between an inner membrane, an outer membrane, and a corresponding bottom ring, positioning ring, and flip ring of the multi-functional soft tissue wound protective sleeve according to the present application.

A medical inner membrane 5 is used to connect the bottom ring 3 and the flip ring 4 and defines a surgery channel 6 (see FIG. 6). In a non-working state, the bottom ring 3 is disposed at a lower portion of the flip ring 4 in a suspending manner in free fall by using the medical inner membrane 5.

A positioning ring 7 is connected to a hole edge of the surgery through-hole 103 on the bottom patch 101 in a sealed manner, a medical outer membrane 8 (see FIG. 6) is connected between the positioning ring 7 and the flip ring 4, and effluent flowing from the surgery channel 6 gets over the flip ring 4, flows through an upper surface of the bottom patch 101 along an outer side of the medical outer membrane 8, and enters the bag. In a working state, after being turned over, the flip ring contacts the positioning ring 7 to tightly clamp the bottom ring and the positioning ring respectively on an inner surface and an outer surface of an abdominal wall of a human body.

Figure 1:
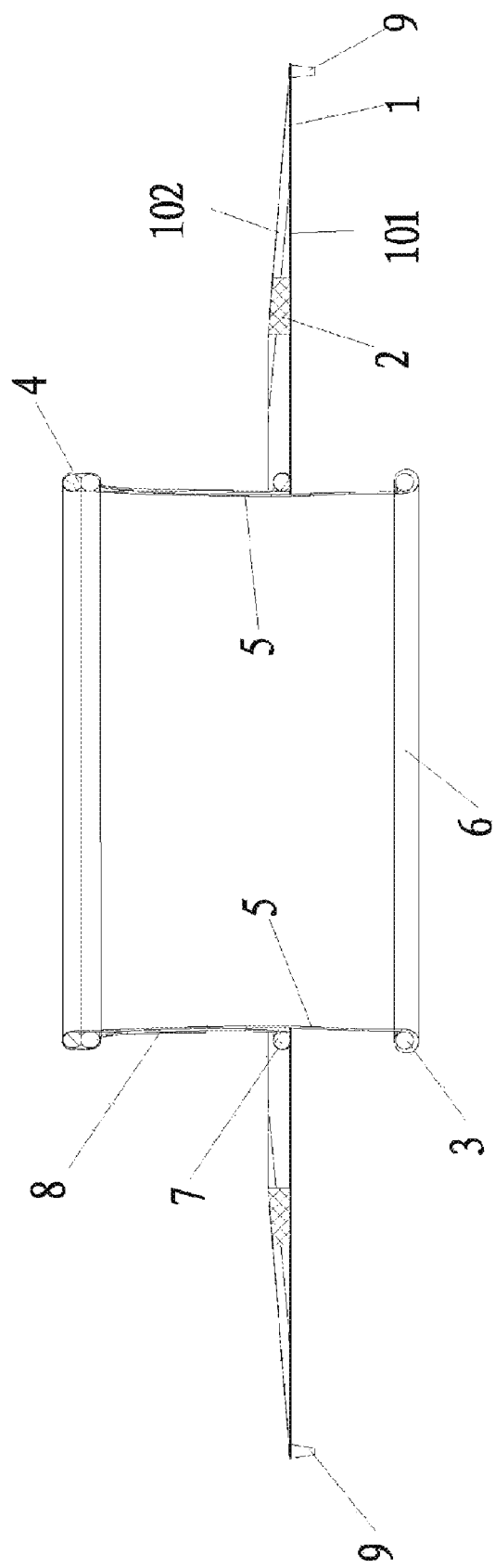
FIG. 1 is a schematic cross-sectional structural diagram of a multi-functional soft tissue wound protective sleeve according to the present application.
Figure 2:
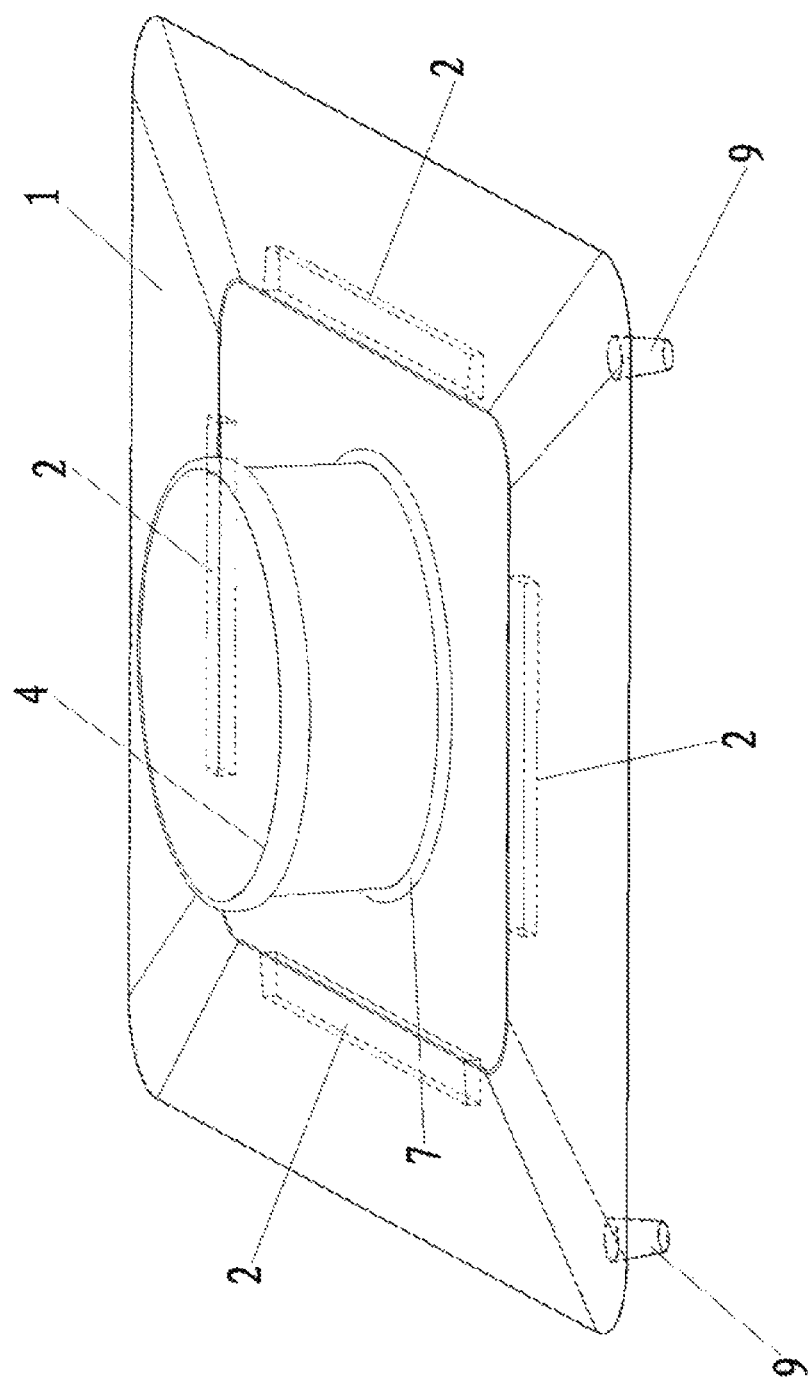
FIG. 2 is a schematic 3D structural diagram of the multi-functional soft tissue wound protective sleeve shown in FIG. 1.
Figure 3:
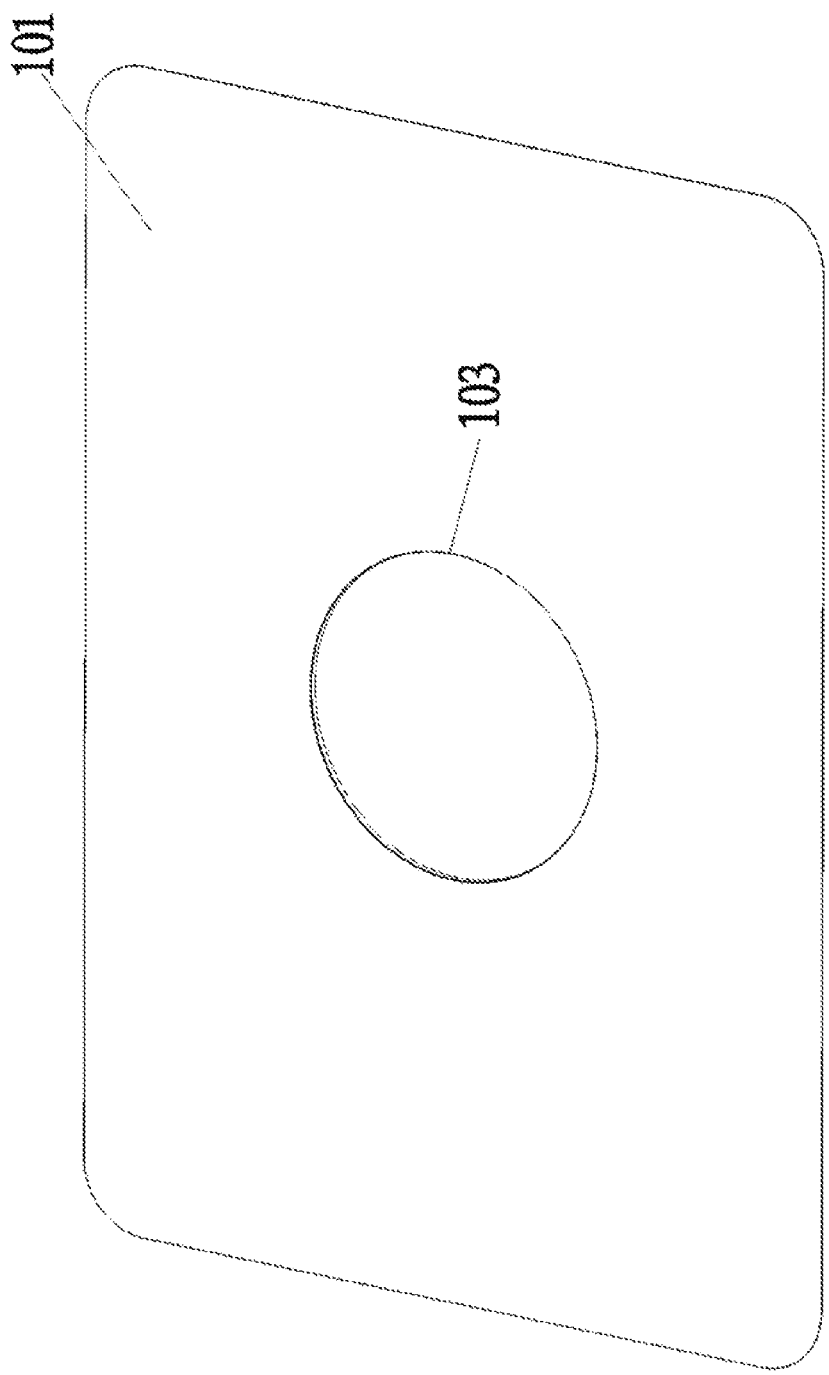
FIG. 3 is a schematic structural diagram of a bottom patch of the multi-functional soft tissue wound protective sleeve according to the present application.
Figure 4:
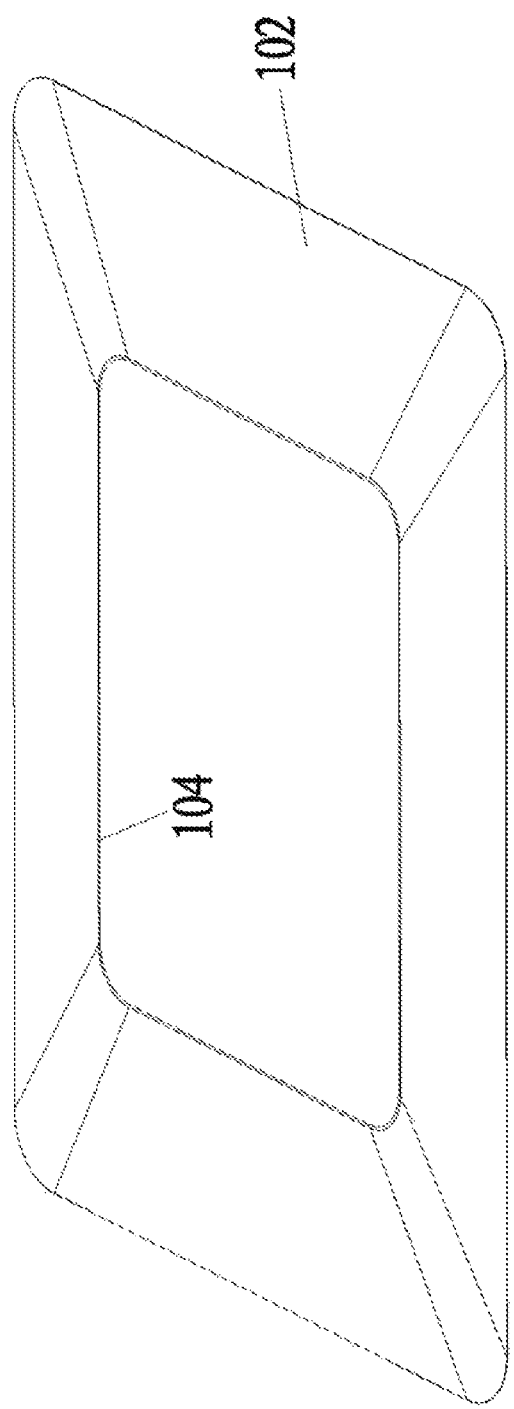
FIG. 4 is a schematic structural diagram of a surface patch of the multi-functional soft tissue wound protective sleeve according to the present application.

A cross-sectional view of a working state protective sleeve consisting of the foregoing components is shown in FIG. 1; a schematic 3D structural diagram of the multi-functional soft tissue wound protective sleeve is shown in FIG. 2.

When leaving a factory, the waste collection bag 1 may be folded upwards, and the bottom ring is in a free suspension state. During a surgery, the bottom ring 3 in a free suspension state may be first placed in an abdominal cavity, to push aside human tissues, then the waste collection bag 1 is opened, and the flip ring is turned over to be in contact with the positioning ring. During a surgery, if a distance between bottom rings is found to be excessively great, the bottom ring may be first turned over, so as to reduce a suspension height and then place the bottom rings into a human body. During a surgical process, effluent flowing from a surgery channel or brought out by a surgical instrument or by medical use directly enters the bag from the opening 104 of the surface patch. Even if the effluent drips on the flip ring, the effluent enters the bag along the medical outer membrane and has no pollution to the environment and the surface of a patient. If overmuch fluid flows out, the fluid may also be discharged in time from the bag by using the diversion component 9 (such as a vacuum extractor).

Parts not involved in the present application are all the same as the prior art or can be implemented by using the prior art.

What is claimed is:

1. A multi-functional soft tissue wound protective sleeve, comprising:
   a waste collection bag including a bottom patch and a surface patch, wherein outer edges of the bottom patch and the surface patch are connected to form a cavity, a surgery through-hole is provided on the bottom patch, and a waste inlet opening is provided on the surface patch;
   a bottom ring configured to be inserted into a human body, wherein the bottom ring is configured to push away human tissues surrounding the bottom ring to form a surgery space;
   a flip ring located above the waste collection bag and having an adjustable distance with the bottom ring, wherein the flip ring is configured to prevent waste from touching a surgical surface;
   a medical inner membrane connecting the bottom ring to the flip ring and defining a surgery channel to the surgery space;
   a positioning ring sealed with a hole edge of the surgery through-hole on the bottom patch; and
   a medical outer membrane connecting the positioning ring to the flip ring, wherein the medical outer membrane guides waste escaping the surgery channel over the flip ring to flow into the waste collection bag.

2. The multi-functional soft tissue wound protective sleeve according to claim 1, wherein a plurality of support blocks is disposed between the bottom patch and the surface patch and deployed around the waste inlet opening of the surface patch to prevent the waste collection bag from closing.

3. The multi-functional soft tissue wound protective sleeve according to claim 2, wherein each support block is a strip sponge filter structure.

4. The multi-functional soft tissue wound protective sleeve according to claim 1, wherein the waste collection bag includes a diversion component to discharge waste accumulated in the waste collection bag.

5. The multi-functional soft tissue wound protective sleeve according to claim 1, wherein the flip ring is a thermoplastic polyurethanes (TPU) ring whose cross section is "8"-shaped.

6. The multi-functional soft tissue wound protective sleeve according to claim 1, wherein the waste inlet opening of the surface patch has a wrinkled structure for waste to flow into the waste collection bag.

7. The multi-functional soft tissue wound protective sleeve according to claim 1, wherein an area of the waste inlet opening is greater than that of the surgery through-hole.

8. The multi-functional soft tissue wound protective sleeve according to claim 1, wherein an inner diameter of the flip ring is less than an inner diameter of the bottom ring.

* * * * *